United States Patent [19]

Arnold

[11] Patent Number: 4,563,896

[45] Date of Patent: Jan. 14, 1986

[54] GAUGER'S AID FOR USE IN SAMPLING BOTTOM SEDIMENT CONDITIONS IN OIL STORAGE TANKS

[75] Inventor: Lewis R. Arnold, Nowata, Okla.

[73] Assignee: Bigheart Pipe Line Corporation, Reno, Nev.

[21] Appl. No.: 549,900

[22] Filed: Nov. 9, 1983

[51] Int. Cl.$^4$ .............................................. G01F 23/00
[52] U.S. Cl. ................... 73/290 R; 73/863.81; 73/864.51; 73/864.63
[58] Field of Search ............... 7/164, 167; 16/110 R, 16/111 R, 114 R; 73/290 R, 319, 863.81, 863.82, 864.31, 864.32, 864.51, 864.63, 864.65, 864.91; 294/19 R, 19 A, 26, 54.5, 57

[56] References Cited

U.S. PATENT DOCUMENTS

| | | | |
|---|---|---|---|
| 1,857,537 | 5/1932 | Frank et al. ................... | 73/864.63 |
| 1,944,392 | 1/1934 | Atkins et al. ................... | 73/864.51 |
| 2,174,100 | 9/1939 | Walker ........................... | 73/864.65 |
| 2,189,238 | 2/1940 | Benjamin ........................ | 73/864.63 |
| 2,376,290 | 5/1945 | Stewart .......................... | 294/26 |
| 2,713,269 | 7/1955 | Neer ............................... | 73/864.65 X |
| 2,783,076 | 2/1957 | Shropshire ..................... | 294/26 X |
| 2,997,878 | 8/1961 | Graham ......................... | 73/290 R X |
| 3,014,749 | 12/1961 | Carrow .......................... | 294/26 |
| 3,078,604 | 2/1963 | Neuman ........................ | 294/54.5 |
| 3,136,574 | 6/1964 | Pasquale ....................... | 16/110 R X |
| 3,169,403 | 2/1965 | McGinn ........................ | 73/864.63 |
| 3,433,521 | 3/1969 | Lasko ............................ | 294/19.1 |
| 3,434,753 | 3/1969 | De Croes ..................... | 294/19.2 |
| 3,464,732 | 9/1969 | Woodward .................... | 294/19.1 |
| 3,841,685 | 10/1974 | Kolodziej ...................... | 294/19.1 |
| 3,960,021 | 6/1976 | Jones ............................. | 73/864.51 |
| 3,960,218 | 6/1976 | Atchley et al. ................. | 294/19.1 X |
| 4,046,413 | 9/1977 | Jeninga ......................... | 294/19.2 |
| 4,121,531 | 10/1978 | Norton .......................... | 294/19.1 X |
| 4,258,447 | 3/1981 | Garcia ........................... | 294/19.1 X |

*Primary Examiner*—Robert Spitzer
*Attorney, Agent, or Firm*—Head, Johnson & Stevenson

[57] ABSTRACT

A tool for use in sampling bottom sediment conditions in oil storage tanks utilizing a thief suspended on a rope. The bottom sediment sample is taken through a thief hatch opening in a tank top adjacent the tank peripheral edge. The tool is an elongated slender member having a U-shaped outer end for receiving the rope, the tool being dimensioned for extension through the tank thief hatch and having an inner end engageable by the user so as to retain the body member generally horizontally within the tank and leave the gauger's hands free so that the thief may be lowered into the tank in areas displaced away from those areas vertically below the thief hatch.

5 Claims, 5 Drawing Figures

GAUGER'S AID FOR USE IN SAMPLING BOTTOM SEDIMENT CONDITIONS IN OIL STORAGE TANKS

SUMMARY OF THE INVENTION

Most crude oil produced in the United States and other areas of the world flows from wells in an oil field to a storage tank. When a tank is full or nearly full the custody of the crude oil in the tank is transferred from the producer to the transporter, usually a pipeline. In order to know the quantity of crude oil being delivered a gauger is employed to measure the depth of fluid within the tank. By means of the measured depth of fluid the volume of fluid can be easily determined. In addition, it is the gauger's responsibility to approve the measured contents for passage from the tank into a pipeline for delivery to a refinery or for other purposes.

The gauger is required to not only determine the quantity of crude oil in the tank which will be conveyed from the tank to a pipeline, he must also determine that the liquid being delivered is in fact crude oil and not water. In addition, the gauger is responsible to determine that the full quantity of the crude oil being transferred is in fact delivered from the tank into the connecting pipeline. For these reasons, the gauger has serious responsibilities. To carry out these responsibility the gauger makes samples of the crude oil at various levels, particularly near the bottom to make sure that the liquid is all crude oil and not crude oil suspended on a layer of water. To make such measurements, the gauger carries with him a device known as a "thief" which is a small closed vessel by which samples may be taken of the liquid and other contents adjacent the bottom of the tank. This thief is lowered into the tank by means of a rope. To permit this to be accomplished, oil storage tanks have an opening in the tank top adjacent the upper peripherial edge. The opening is termed a "thief hatch opening" since it is typically covered by a lid or "hatch". The gauger opens the thief hatch and lowers the thief on a rope into the tank to check for water and in addition, to check for bottom sediment in the tank.

Most all crude oil includes some physical material carried with it such as sand from the producing formation, rust, and so forth. This material tends to settle out of the crude oil when the crude oil is delivered into a tank and is termed "bottom sediment", or as abbreviated in the trade, "BS". Since some BS is expected in the bottom of all crude oil tanks which have been in use for a period of time, the pipeline which is used to draw the fluid out of the tank is not placed in the bottom but is placed somewhat above the tank bottom leaving an area in the bottom of the tank which is never drained during the normal course of transferring custody of crude oil in the tank from the producer to a pipeline. This allows the bottom sediment to accumulate below this outlet line and as long as the sediment are below such outlet line there is no affect on the quantity of crude oil delivered. However, if the bottom sediment build up to a level above the level of the outlet delivery line then the heighth of crude oil within the tank is not a proper indication of the volume of liquid which will be delivered when the tank is drained down to the level of the outlet delivery line. For this reason the gauger must make sure that the bottom sediment do not extend above a certain elevation in the tank.

Since the thief hatch must be adjacent the tank periphery in order for the gauger to reach it the typical means of gauging is to lower the thief directly below the thief hatch and that is, adjacent the peripherial wall of the tank. Some producers can deceive the gauger by using a long pole or paddle to move the bottom sediments away from the area immediately below the thief hatch towards the center of the tank or towards the opposite side. Thus if the gauger is not suspecting, he will lower the thief directly below the thief hatch and conclude that the bottom sediments are at an acceptable level whereas, in fact, the bottom sediments may extend above the accepted level in other areas of the tank.

The present invention is directed toward a simple device which can be utilized by the gauger to position the thief at various areas within the tank disposed away from that immediately below the thief hatch.

The invention is a gauger's aid which can be carried by the gauger and extended into the tank. The aid in the form of an elongated member having a U-shaped outer end to slideably receive the rope attached to the thief. The inner end remains exteriorly of the tank. In the preferred arrangement the inner end has a horizontal bar so that the gauger may lean against the horizontal bar with his stomach, thereby causing the elongated body member to extend generally horizontally within the tank. The gauger's hands are then free to raise and lower the thief on the end of a thief rope so that he can determine whether or not the bottom sediments are acceptable even in areas of the tank which are displaced away from the area immediately below the thief hatch.

DESCRIPTION OF THE DRAWING

FIG. 1 shows the gauger's aid of this invention utilized to position a thief in the tank.

DETAILED DESCRIPTION OF THE PREFERRED EMBODIMENT

Figure 1:
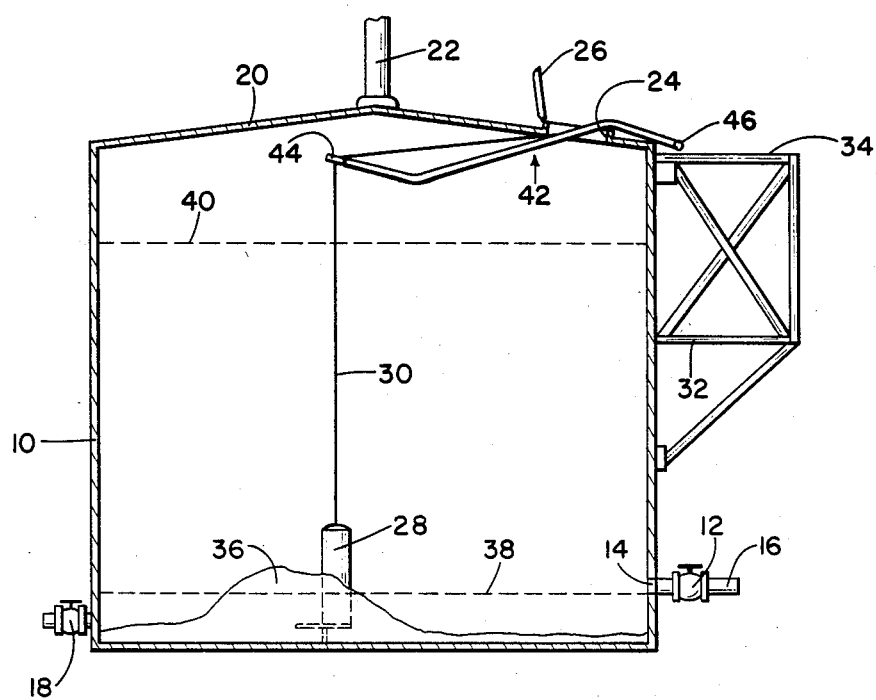
FIG. 1 is a cross-sectional view of an oil storage tank in which crude oil is stored as it is produced in an oil field and before custody of the oil is transferred from the producer to a pipeline.

Referring to the drawing and first to FIG. 1 a tank 10 is illustrated as being of the type typically employed for receiving crude oil produced in an oil field. Crude oil is received and stored in tank 10 until it is time to transfer custody of the oil therein to a pipeline. Since crude oil is relatively expensive and valuable material, and is handled in large quantities, it is important that great accuracy be maintained in determining the quantity of crude oil being conveyed from tank 10 to a pipeline.

A header valve 12 is connected by a line to an opening 14 in the tank. From valve 12 line 16 typically connects to a pipeline. When the crude oil passes through valve 12 custody is typically transferred from the producer to the pipeline.

A drain-off valve 18 is also illustrated for use in draining the tank 10 however the drain-off valve is not utilized in transferring custody and must remain closed during the period from the time the tank is gauged until the contents thereof have been drained through the header valve 12.

The tank 10 typically has a closed top 20 to keep out rain water, to decrease evaporation of the gas content of the crude oil and for safety purposes. Crude oil flows into the tank through an inlet pipe 22 which either may be on the top of the tank as illustrated or in the sidewall of the tank adjacent the top.

Near one vertical sidewall of the tank is an opening 24 which is provided specifically for use by the gauger and is termed a thief opening 24. This is typically closed by a cover 26 when the opening is not in use. The opening 24 and cover 26 are typically referred to in combination as a thief hatch.

The gauger in determining that conditions are proper for the transfer of custody of the crude oil must make his investigation through the thief hatch opening 24. This is customarily done by use of a thief 28 suspended on a rope 30. The thief 28 is a cylindrical vessel for gathering samples and is well known and has been employed for many years in the industry and will not be described in further detail since the specific design of the thief is not relevant to the invention.

Typically tank 10 includes a walkway 32 surrounded by handrails 34 for safety. A ladder (not shown) extends from the ground to the walkway. When the gauger opens the thief hatch 26 the gauger lowers the thief 28 by means of rope 30 directly vertically downwardly into the interior of tank 10. Shown in the tank 10 is a pile of bottom sediments or BS 36. This physical material is an inevitable part of most crude oil production and tends to settle out within crude storage tank. It is the function and responsibility of the gauger to make sure that the BS does not rise to a level which would cause a false indication of the quantity of fluid being delivered. For instance, when the header valve 12 is opened the crude oil will flow out through line 16 down to the level indicated by the dotted line 38. If the BS 36 is below line 38 then it has no effect on the quantity of oil being delivered from the tank 10 regardless of how high the crude oil is at the time delivery starts above the line 38 since the measurements made by the gauger are predicated upon the oil being emptied from the tank to the level indicated by line 38. If the gauger lowers the thief 28 directly below thief hatch opening 24 he would conclude that condition as far as BS is concerned is satisfactory, whereas in fact, the quantity of oil which would be delivered when the tank is drained from the beginning level (indicated by the dotted line 40) to the bottom level (indicated by the dotted line 38) will be less the volume of BS extending above line 38.

This invention provides a means of enabling the gauger to make a more accurate determination of BS conditions.

Figure 2:
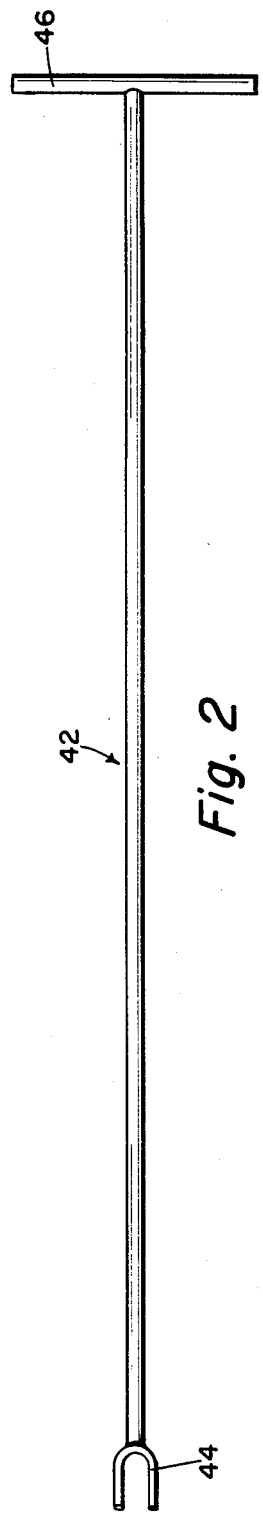
FIG. 2 is a top view of the gauger's aid of this invention.
Figure 3:
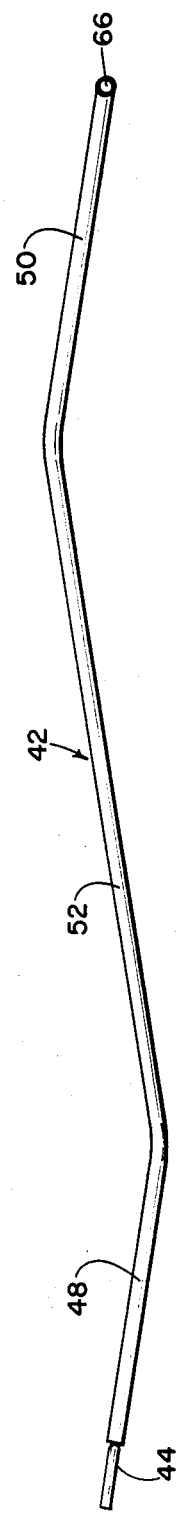
FIG. 3 is a side elevational view of the gauger's aid of FIG. 2.

The invention is illustrated best in FIGS. 2 and 3 and includes a tool having an elongated slender body generally indicated by the numeral 42. At the outer end of the body member 42 is a U-shaped member 44 dimensioned so as to freely pass through the thief hatch opening 24. The U-shaped member 44 is configured to receive rope 30 as shown in FIG. 1 in a sliding relationship so that the thief can be raised and lowered by the rope passing up or down through the U-shaped member 44.

At the opposite end of the body member 42 is a handle member 46 in the form of a rod extending transversely of the body member. Handle member 46 may be welded to the outer end of the body member. The handle member 46 is preferably of length exceeding the longest dimension of the typical thief hatch 24 so as to help prevent the tool from falling into the interior of the tank. Further, the handle member 46 is configured so that in use, the gauger can stand before the thief hatch with the tool body member 42 extending generally horizontally within the tank as shown in FIG. 1 and in which condition the gauger can lean against the handle member 46 with his stomach to hold the tool in the proper position. This enables both hands of the gauger to be free to raise and lower rope 30.

While the tool may be completely straight, the preferred as illustrated in FIGS. 1 and 3 is that in which the body member 42 is formed of three portions. The first portion 48 and the second portion 50 are at the opposed ends of the tool and are generally in planes parallel and displaced from each other. At the outer end of the first body portion 48 is the U-shaped member 44 and at the outer end of the second body portion 50 is the handle member 46. Integrally connecting the first and second body portions 48 and 50 is an intermediate portion 52. The configuration of FIG. 3, which is also shown in FIG. 1, expedites the handling of the rope and thief 28 within the tank.

It can be seen that with the use of the tool a gauger can extend the positioning of the thief 28 to various portions of the interior of the tank to thereby assure himself that all areas of the tank are acceptable for delivery of crude oil and not just that area immediately below the thief hatch opening 24.

Figure 5:
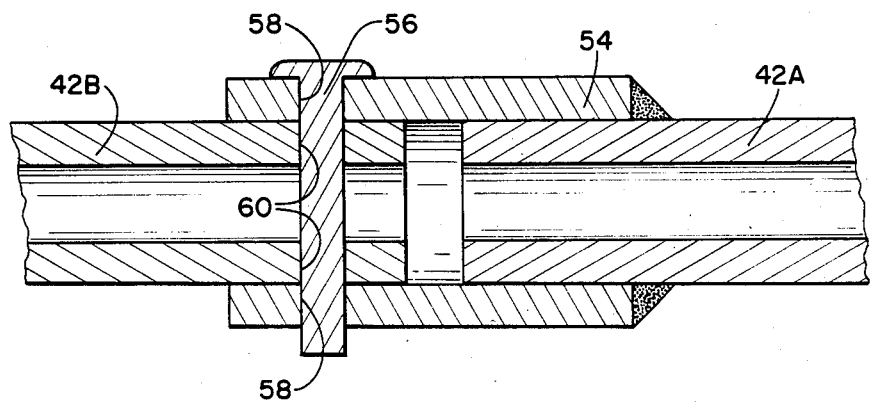
FIG. 5 is an enlarged cross-sectional view of FIG. 4 showing the means for separating the gauger's aids into two portions.
Figure 4:
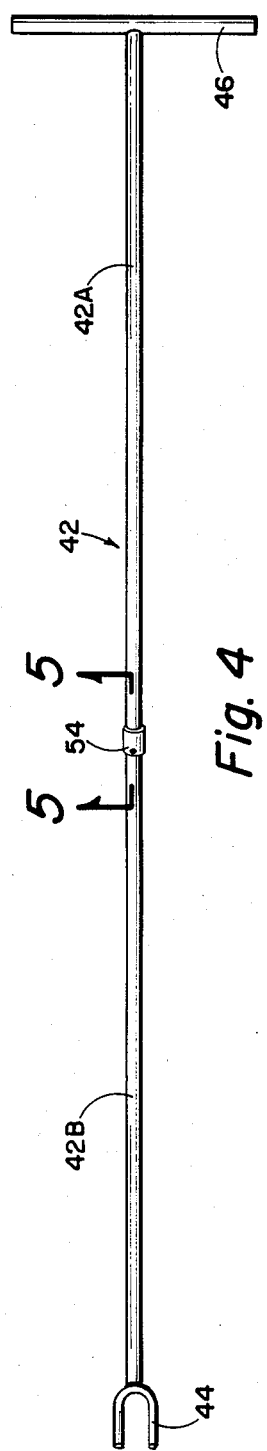
FIG. 4 is a view as in FIG. 1 but showing an alternate embodiment of the invention wherein the gauger's aid may be separated into two portions to facilitate carrying the gauger's aid in a car or pick-up.

To facilitate transporting the tool an embodiment is shown in FIGS. 4 and 5 which can be used to reduce the overall length of the tool when it is not being used. In this case the body portion 42 is formed of two parts indicated by 42A and 42B. In any event, the portion 42A has secured at the outer end a tubular member 54 which remains permanently attached. The other body portion 42B is telescopically received within the tubular member 54 so that it can be separated from it. By means of a pin 56 extending through openings 58 in the tubular member and 60 in the body portion 42B, the body portions can be held together when in use. It can be seen that instead of the use of pin 56, the interior of the tubular member 54 could be threaded and the exterior of the body portion 42B threaded and these members secured to each other in this manner.

The gaugers aid should preferably be made of aluminum, wood, fiberglass or other material which will not cause a spark when contacting any portion of the tank in which it is used.

The invention thus shows a relatively simple device for enabling a gauger charged with the responsibility of approving the transfer of custody of crude oil from a a storage tank to more accurately determine that bottom sediments will not cause an inaccurate measurement.

In FIGS. 3 and 5 the length of tubular member 54 is illustrated as being relatively short. In practical use of the invention it should be long enough to safely support the portions 42A and 42B. For example, if the diameter of portions 42A and 42B is about three-fourths inch then tubular member 54 should be about four inches long or longer.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A gauger's system for use in sampling bottom sediment conditions in an oil storage tank in which a sample is taken through a thief latch opening in the tank top, the opening being adjacent the tank peripheral edge, comprising:

a thief having means for taking a sample of bottom sediment;

a rope, said thief being secured to one end thereof;

a tool having an elongated slender body member of a length to extend through a thief hatch opening in a tank top and to at least about the central vertical axis of the tank for which it is dimensioned;

a forked member on the end of said tool body member dimensioned to be passed through a tank thief hatch opening, the forked member adaptable to slideably receive said rope having said thief at the end thereof; and a handle member on the other end of said tool body member, the handle member extending transversely of said body member and configured to be engaged by the user to cause said body member to extend generally horizontally within a tank to permit the user to manipulate said rope to raise and lower said thief in a tank.

2. A gauger's system according to claim 1 wherein said body member is formed of three portions, the first and third portions being generally straight and in parallel planes displaced from each other and the intermediate portion extending at an angle to and connecting said first and second portions, said forked member being on the end of said third body portion and said handle member being affixed to the end of said first body portion.

3. A gauger's system according to claim 1 wherein said handle member is a generally straight slender member affixed adjacent its longitudinal center to said body member.

4. A gauger's system according to claim 3 wherein said handle member is configured and dimensioned to be engaged by the stomach of the user to maintain the tool generally horizontally within a tank and permit the users hands to be free to operate said rope to raise and lower said thief.

5. A gauger's system according to claim 1 wherein said handle member is of a length greater than the longest dimension of said tank thief hatch opening whereby the possibility of the tool falling into a tank is reduced.

* * * * *